US006416763B1

(12) United States Patent
McDonell et al.

(10) Patent No.: US 6,416,763 B1
(45) Date of Patent: Jul. 9, 2002

(54) RECOMBINANT NONSTRUCTURAL PROTEIN SUBUNIT VACCINE AGAINST FLAVIVIRAL INFECTION

(75) Inventors: Michael McDonell, Kailua; Iain Peters, Honolulu; Beth-Ann Coller, Aiea, all of HI (US)

(73) Assignee: Hawaii Biotechnology Group, Inc., Aeia, HI (US)

( * ) Notice: Subject to any disclaimer, the term of this patent is extended or adjusted under 35 U.S.C. 154(b) by 0 days.

(21) Appl. No.: 09/143,077

(22) Filed: Aug. 28, 1998

(51) Int. Cl.[7] ................................................ A61K 39/12

(52) U.S. Cl. ................................ 424/218.1; 424/186.1; 424/202.1; 435/5; 435/69.1; 435/69.3

(58) Field of Search ............................ 435/5, 7.1, 69.1, 435/69.3; 424/184.1, 186.1, 202.1, 206.1, 218.1

(56) References Cited

U.S. PATENT DOCUMENTS

| | | | | |
|---|---|---|---|---|
| 4,399,216 A | | 8/1983 | Axel et al. | 435/6 |
| 5,494,671 A | * | 2/1996 | Lai et al. | 424/218.1 |

FOREIGN PATENT DOCUMENTS

| | | |
|---|---|---|
| WO | WO 90/14837 | 12/1990 |
| WO | WO 9202548 A | 2/1992 |
| WO | WO 92 03161 A | 3/1992 |
| WO | WO 9637221 A | 11/1996 |

OTHER PUBLICATIONS

Schlesinger, J. J., et al., 1987, "Protection of mice against dengue 2 virus encephalitis by immunization with the dengue 2 virus non–structural glycoprotein NS1", J. Gen. Virol. 68:853–857.*

Men, R., et al., 1991, "Carboxy–terminally truncated dengue virus envelope glycoproteins expressed on the cell surface and secreted extracellularly exhibit increased immunogenicity in mice", J. Virol. 65(3):1400–1407.*

Patarapotikul, J., et al., 1993, "Western blot analysis of antigens specifically recognized by natural immune responses of patients with Japanese encephalitis infections", Southeast Asian J. Trop. Med. Pub. Health 24(2):269–276.*

Cardosa, M. J., 1998, "Dengue vaccine design: issues and challenges", Brit. Med. Bull. 54(2):395–405.*

Bancroft, W. H., 1987, "Current status of dengue vaccines and prospects for the future", PRHSJ 6(1):23–26.*

Lai, C. J., et al., 1998, "Evaluation of molecular strategies to develop a live dengue vaccine", Clin. Diag. Virol. 10:173–179.*

Culp, J. S. et al., 1991, "Regulated expression allows high level production and secretion of HIV–1 gp120 envelope glycoprotein in Drosophila Schneider cells", Bio/Technol. 9:173–177.*

Bray, M. et al., Mice Immunized With Recombinant Vaccinia Virus Expressing Dengue 4 Virus Structural Proteins With Or Without Nonstructural Protein NS1 Are Protected Against Fatal Dengue Virus Encephalitis, J. Virol., (1989) 63(6):2853–6.

Cane, P. A. et al., Reduction Of Yellow Fever Virus Mouse Neurovirulence By Immunization With A Bacterially Synthesized Non–Structural Protein (NS1) Fragment, J. Gen. Virol., (1988) 69:1241–6.

Chambers, T. J. et al., Flavivirus Genome Organization, Expression, And Replication, Annu. Rev. Microbiol., (1990) 44: 649–88.

Crooks, A. J. et al., The NS1 Protein Of Tick–Borne Encephalitis Virus Forms Multimeric Species Upon Secretion From The Host Cell, J. Gen. Virol., (1994) 75:3453–60.

Eckels, K. H. et al., Dengue–2 Vaccine: Preparation From A Small–Plaque Virus Clone, Infect. Immun., (1980) 27(1): 175–80.

Falconar, A.K.I. et al., Immunoaffinity Purification Of Native Dimer Forms Of The Flavivirus Non–Structural Glycoprotein, NS1, J. Virol. Meth., (1990) 30:323–32.

Falgout, B. et al., Immunization Of Mice With Recombinant Vaccinia Virus Expressing Authentic Dengue Virus Nonstructural Protein NS1 Protects Against Lethal Dengue Virus Encephalitis, J. Virol., (1990) 64(9):4356–63.

Falgout, B. et al., Proper Processing Of Dengue Virus Nonstructural Glycoprotein NS1 Requires The N–Terminal Hydrophobic Signal Sequence And The Downstream Nonstructural Protein NS2a., J. Virol., (1989) 63(5):1852–60.

Feighny, R. et al., Purification Of Native Dengue–2 Viral Proteins And The Ability Of Purified Proteins To Protect Mice, Am. J. Trop. Med. Hyg., (1992) 47(4):405–12.

Hahn, Y. S. et al., Nucleotide Sequence Of Dengue 2 RNA And Comparison Of The Encoded Proteins With Those Of Other Flaviviruses., Virol., (1988) 162:167–80.

Hall, R. A. et al., Protective Immune Responses To The E And NS1 Proteins Of Murray Valley Encephalitis Virus In Hybrids Of Flavivirus–Resistant Mice, J. Gen. Virol., (1996) 77:1287–94.

(List continued on next page.)

*Primary Examiner*—Laurie Scheiner
*Assistant Examiner*—Jeffrey S. Parkin
(74) *Attorney, Agent, or Firm*—Morrison & Foerster LLP

(57) ABSTRACT

The recombinant expression and secretion from eucaryotic host cells, particularly Drosophila cells, of Flavivirus nonstructural (NS) protein, particularly NS1, is useful in combination with Flavivirus truncated envelope (E) protein to protect a host subject from infection and disease from Flavivirus species. Further, NS1 is useful as a diagnostic of flaviviral infection.

Compositions of truncated flaviviral envelope protein and flaviviral nonstructural protein induce high titer virus neutralizing antibodies believed to be important in protection against flaviviral infection and which are useful in diagnosis of infection by the virus.

14 Claims, 8 Drawing Sheets

OTHER PUBLICATIONS

Halstead, S. B., Pathogenesis Of Dengue: Challenges To Molecular Biology, Science, (1988) 239:476–81.
Hsieh, P. et al., Regulation Of Asparagine–Linked Oligosaccharide Processing, J. Biol. Chem. (1984) 259(4):2375–82.
Jacobs, S. C. et al., Protection Elicited By Replication–Defective Adenovirus Vector Expressing The Tick–Borne Encephalitis Virus Non–Structural Glycoprotein NS1, J. Gen. Virol., (1994) 75:2399–402.
Kaufman, R. J. Selection And Coamplification Of Heterologous Genes In Mammalian Cells, Meth. Enzymol., (1990) 185:537–66.
Konishi, E. et al., Comparison Of Protective Immunity Elicited By Recombinant Vaccinia Viruses That Synthesize E Or NS1 Of Japanese Encephalitis Virus, Virol., (1991) 185:401–10.
Leblois, H. et al., Maturation Of The Dengue–2 Virus NS1 Protein In Insect Cells: Effects Of Downstream NS2A Sequences On Baculovirus–Expressed Gene Constructs, J. Gen. Virol., (1995) 76:979–84.
Lin, Y. et al., DNA Immunization With Japanese Encephalitis Virus Nonstructural Protein NS1 Elicits Protective Immunity In Mice, J. Virol., (1998) 72(1):191–200.
Lindenbach, B. D. et al., Trans–Complementation Of Yellow Fever Virus NS1 Reveals A Role In Early RNA Replication, J. Virol., (1997) 71(12):9608–17.
Mackenzie, J. M. et al., Immunolocalization Of The Dengue Virus Nonstructural Glycoprotein NS1 Suggests A Role In Viral RNA Replication, Virol., (1996) 220:232–40.
McCown, J. et al., Protection Of Mice Against Lethal Japanese Encephalitis With A Recombinant Baculovirus Vaccine, Am. J. Trop. Med. Hygene, (1990) 42(5):491–99.
Muylaert, I. R. et al., Genetic Analysis Of The Yellow Fever Virus NS1 Protein: Identification Of A Temperature–Sensitive Mutation Which Blocks RNA Accumulation, J. Virol., (1997) 71(1):291–98.
Putnak, J. R. et al., Protection Of Mice Against Yellow Fever Virus Encephalitis By Immunization With A Vaccinia Virus Recombinant Encoding The Yellow Fever Virus Non–Structural Proteins, NS1, NS2a And NS2b, J. Gen. Virol., (1990) 71:1697–702.
Qu, X. et al., Immunoreactivity And Protective Effects In Mice Of A Recombinant Dengue 2 Tonga Virus NS1 Protein Produced In A Baculovirus Expression System, J. Gen. Virol., (1993) 74:89–97.
Schlesinger, J. J. et al., Protection Against Yellow Fever In Monkeys By Immunization With Yellow Fever Virus Nonstructural Protein NS1, J. Virol., (1986) 60(3):1153–55.
Schlesinger, J. J. et al., Cell Surface Expression Of Yellow Fever Virus Non–Structural Glycoprotein NS1: Consequences Of Interaction With Antibody., J. Gen. Virol. (1990) 71:593–99.
Schlesinger, J. J. et al., Protection Against 17D Yellow Fever Encephalitis In Mice By Passive Transfer Of Monoclonal Antibodies To The Nonstructural Glycoprotein gp48 And By Active Immunization With gp48, J. Immunol., (1985) 135(4):2805–9.
Schlesinger, J. J. et al.,Protection Of Mice Against Dengue 2 Virus Encephalitis By Immunization With The Dengue 2 Virus Non–Structural Glycoprotein NS1, J. Gen. Virol., (1987) 68:853–7.
Schlesinger, J. J. et al.,The Fc Portion Of Antibody To Yellow Fever Virus NS1 Is A Determinant Of Protection Against YF Encephalitis In Mice, Virol., (1993) 192:132–41.
Smith, G. W. et al., Synthesis of Proteins and Glycoproteins in Dengue Type 2 Virus–Infected Vero and Aedes Albopictus Cells., J. Gen. Virol., (1985) 66:559–71.
Tan, B. H. et al., Recombinant Dengue Type 1 Virus NS5 Protein Expressed In *Escherichia Coli* Exhibits RNA–Dependent RNA Polymerase Activity, Virol., (1986) 216:317–25.
Van Der Straten, A. et al., Introduction And Constitutive Expression Of Gene Products In Cultured Drosophila Cells Using Hygromycin B Selection, Meth. Mol. Cell. Biol., (1989) 1(1):1–18.
Wigler, M. et al., Transformation Of Mammalian Cells With Genes From Procaryotes And Eucaryotes, Cell, (1979) 16: 777–85.
Winkler, G. et al., Evidence That The Mature Form Of The Flavivirus Nonstructural Protein NS1 Is A Dimer, Virol. (1988) 162:187–96.
Search Report for International Application No. PCT/US99/19707 dated May 16, 2000.
Feighny et al., (1992) "Purification of Native Dengue–2 Viral Proteins and the Ability of Purifie Proteins to Protect mice" American Journal of Tropical Medicine and Hygiene, vol. 47, No. 4 pp. 405–412.
Crooks, et al. (1994) "The NSI Protein of Tick–borne Encephalitis Virus Forms Multimeric Species Upon Secretion from the Host Cell" Journal of General Virology, vol. 75, No. 12, pp 3453–3460.
Patent Cooperation Treaty International Search Report for PCT/US99/19707.
Despres, P. et al. (1991). "Recombinant Baculoviruses Expressing Yellow Fever Virus E and NS1 Proteins Elicit Protective Immunity in Mice," *Journal of General Virology* 72:2811–2816.

* cited by examiner

D2NS1.2422p (upstream)

Bgl II

5'-cttctagatctcgagtacccgggacc GAT AGT GGT TGC GTT G-3'

XbaI XhoI SmaI

D2NS1.3477m (downstream)

SalI

5'-gctctagagtcga cta tta GGC TGT GAC CAG AGA AC-3'

XbaI End End

FIG. 1

SEQUENCE LISTING

```
<160> NUMBER OF SEQ ID NOS: 3

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:  PCR primer
      used to clone NS1.

<400> SEQUENCE: 1

cttctagatc tcgagtaccc gggaccgata gtggttgcgt t                        41


<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:  PCR primer
      used to clone NS1.

<400> SEQUENCE: 2

gctctagagt cgactattag gctgtgacca gagaac                              36


<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence:  Predicted
      sequence and processing of primary translation
      product.

<400> SEQUENCE: 3

Leu Leu Leu Cys Gly Ala Val Pro Val Ser Pro Gln Ser Gln Glu Ile
  1               5                  10                  15

His Ala Arg Phe Arg Arg Gly Ala Arg Ser Arg Val Pro Gly Thr Asp
             20                  25                  30

Ser Gly Cys Val
         35
```

RECOMBINANT NONSTRUCTURAL PROTEIN SUBUNIT VACCINE AGAINST FLAVIVIRAL INFECTION

TECHNICAL FIELD

This invention relates to protection against and diagnosis of flaviviral infection. More specifically, this invention concerns recombinantly produced subunits of a nonstructural flaviviral protein that is expressed and secreted as a mature polypeptide from eucaryotic cells. Compositions of truncated flaviviral envelope protein in combination with flaviviral nonstructural protein induce a higher degree of protection against flaviviral infection than the truncated protein alone. These compositions may be useful in the prevention, diagnosis or treatment of flaviviral infection. The present invention relates to compositions of matter and methods of making and methods of using said compositions as well as pharmaceutical compositions and methods of treating using said pharmaceutical compositions as well as diagnostic compositions, methods of making and methods of using said diagnostic compositions. The present invention is further useful as a vaccine for immunoprophylaxis.

Several publications are referenced in the present application. Full citation to these references is found at the end of the specification immediately preceding the claims or where the publication is mentioned. Each of these publications is hereby incorporated herein by reference. Said publications relate to the art to which this invention pertains.

BACKGROUND ART

The family Flaviviridae includes the Japanese encephalitis virus (JE), Tick-borne encephalitis virus (TBE), West Nile virus (WN), dengue virus (including the four serotypes of: DEN-1, DEN-2, DEN-3, and DEN4), and the family prototype, yellow fever virus (YF). In the case of dengue, the viruses are transmitted to man by mosquitoes of the genus Aedes, primarily *A. aegypti* and *A. albopictus*. The viruses cause an illness manifested by high fever, headache, aching muscles and joints, and rash. Some cases, typically in children, result in a more severe forms of infection, dengue hemorrhagic fever and dengue shock syndrome (DHF/DSS), marked by severe hemorrhage, vascular permeability, or both, leading to shock. Without diagnosis and prompt medical intervention, the sudden onset and rapid progression of DHF/DSS can be fatal.

Flaviviruses are the most significant group of arthropod-transmitted viruses in terms of global morbidity and mortality with an estimated one hundred million cases of dengue fever occurring annually Halstead, S. B. 1988. Pathogenesis of Dengue: Challenges to Molecular Biology *Science* 239:476–481. With the global increase in population and urbanization especially throughout the tropics, and the lack of sustained mosquito control measures, the mosquito vectors of flavivirus have distributed throughout the tropics, subtropics, and some temperate areas, bringing the risk of flaviviral infection to over half the world's population. Modern jet travel and human emigration have facilitated global distribution of dengue serotypes, such that now multiple serotypes of dengue are endemic in many regions. Accompanying this in the last 15 years has been an increase in the frequency of dengue epidemics and the incidence of DHF/DSS. For example, in Southeast Asia, DHF/DSS is a leading cause of hospitalization and death among children (Hayes and Gubler, 1992, *Pediatr. Infect. Dis. J.* 11:311-317).

Flaviviruses are small, enveloped viruses containing a single, positive-strand, genomic RNA, approximately 10,500 nucleotides in length containing short 5' and 3' untranslated regions, a single long open reading frame, a 5' cap, and a nonpolyadenylated 3' terminus. The complete nucleotide sequence of numerous flaviviral genomes, including all four DEN serotypes and YF virus have been reported (Fu, J. et al., 1992 *Virology* 188:953–958; Deubel, V. et al., 1986, *Virology* 155:365–377; Hahn, Y. S. et al., 1988, *Virology* 162:167–180; Osatomi, K. et al., 1990, *Virology* 176:643–647; Zhao, B. E. et al., 1986, *Virology* 155:77–88; Mackow, E. et al., 1987, *Virology* 159:217–228; Rice, C. M. et al., 1985, *Science* 229:726–733). All flaviviral proteins are derived from a single long polyprotein through precise processing events mediated by host as well as virally encoded proteases. The ten gene products encoded by the single open reading frame are translated as a polyprotein organized in the order, capsid (C), 'preMembrane' (prM, which is processed to 'Membrane' (M) just prior to virion release from the cell) and 'envelope (E)'; following this are the non-structural (NS) proteins: NS1, NS2a, NS2b, NS3, NS4a, NS4b and NS5 (reviewed in Chambers, Thomas J., Chang S. Hahn, Ricardo Galler, and Charles M. Rice. 1990. Flavivirus Genome Organization, Expression, and Replication. *Ann. Rev. Microbiol.* 44: 649–688; Henchal, Erik A., and J. Robert Putnak. 1990. The Dengue Virus. *Clin. Microbiol. Rev.* 3 (4): 376–396). A stretch of hydrophobic residues at the C-terminal end of E serve both as its membrane anchor as well as signal sequence directing NS1 for translocation into the endoplasmic reticular lumen. Thus precise cleavage at the E-NS1 junction is provided by host signal peptidase Falgout, B., R. Chanock, and C.-J. Lai. 1989. Proper Processing of Dengue Virus Nonstructural Glycoprotein NS1 Requires the N-Terminal Hydrophobic Signal Sequence and the Downstream Nonstructural Protein NS2a. *J. Virol.* 63: 1852–60), while the virally-encoded protease NS2a is responsible for processing at the NS1 C-terminus Leblois, H., and P. R. Young. 1995. Maturation of the Dengue-2 Virus NS1 Protein in Insect Cells: Effects of Downstream NS2A Sequences on Baculovirus-expressed Gene Constructs. *J. Gen. Virol.* 76: 979–984). A role for NS1 in replication of viral RNA is suggested by immunolocalization studies which demonstrate its association with the replicative form dsRNA Mackenzie, J. M., M. K. Jones, and P. R. Young. 1996. Immunolocalization of the Dengue Virus Nonstructural Glycoprotein NS1 Suggests a Role in Viral RNA Replication. *Virol.* 220: 232–240) as well as blockage of RNA accumulation by a temperature-sensitive NS1 mutation Muylaert, I. R., R. Galler, and C. M. Rice. 1997. Genetic Analysis of the Yellow Fever Virus NS1 Protein: Identification of a Temperature-Sensitive Mutation which Blocks RNA Accumulation. *J. Virol* 71: 291–98). Further studies utilizing gene complementation in order to provide the NS1 functions in trans have more precisely definedits role in RNA replication to be just prior to or at initiation of minus-strand synthesis Lindenbach, B. D. and C. M. Rice. 1997. Trans-Complementation of Yellow Fever Virus NS1 Reveals a Role in Early RNA Replication. *J. Virol* 71: 9608–17). Meanwhile, work of others has indicated that the RNA-dependent RNA polymerase activity necessary for viral nucleic acid replication is provided by NS5 Tan, B. H., J. Fu, R. J. Sugrue, E. H. Yap, Y. C. Chan and Y. H. Tan. 1996. Recombinant Dengue Type 1 Virus NS5 Protein Expressed in *Escherichia coli* Exhibits RNA-Dependent RNA Polymerase Activity. *Virology* 216: 317–25).

Processing of the encoded polyprotein is initiated cotranslationally, and full maturation requires both host and virally-encoded proteases. The sites of proteolytic cleavage in the YF virus have been determined by comparing the nucleotide sequence and the amino terminal sequences of the viral proteins. Subsequent to initial processing of the polyprotein, prM is converted to M during viral release (Wengler, G. et al., 1989. *J. Virol* 63:2521–2526) and anchored C is processed during virus maturation (Nowak et al., 1987. *Virology* 156:127–137). The envelope of flaviviruses is derived from the host cell membrane and is decorated with virally-encoded transmembrane proteins membrane (M) and envelope (E). While mature E protein and the precursor to M, prM, are glycosylated, the much smaller mature M protein is not. The E glycoprotein, which is the largest viral structural protein, contains functional domains responsible for cell surface attachment and intraendosomal fusion activities. It is also a major target of the host immune system, inducing virus neutralizing antibodies, protective immunity, as well as antibodies which inhibit hemagglutination.

While all dengue viruses are antigenically related, antigenic distinctions exist that define the four dengue virus serotypes. Infection of an individual with one serotype does not apparently provide long-term immunity against the other serotypes. In fact, secondary infections with heterologous serotypes are becoming increasingly prevalent as multiple serotypes co-circulate in a geographic area. In general, primary infections elicit mostly IgM antibodies directed against type-specific determinants. On the other hand, secondary infection by a heterologous serotype is characterized by IgG antibodies that are flavivirus crossreactive. Consecutive infection with different serotypes is thought to be a major factor contributing to DHF.

Many studies have established the effectiveness of immunoprophylaxis with properly folded flavivirus envelope protein in the prevention of disease in several host subject animal models. However, vaccination against dengue is complicated by observations of enhanced infection associated with the presence of virion-reactive antibodies at subneutralizing concentrations or of non-neutralizing specificity. This antibody-dependent enhancement (ADE) pathway is thought to account for high incidence of the often fatal hemorrhagic fever and shock syndrome forms of dengue occurring in children possessing immunity to a dengue serotype not matching the current infection (Halstead, '88 supra). This has prompted several workers to investigate the potential of Flaviviridae vaccines based on nonstructural proteins, since antibodies reactive against these viral proteins are unlikely to enhance virion entry into monocytes via their IgG constant (Fc) domain receptors, the suspected route of ADE (Halstead, '8 supra). Immunization with NS1 has yielded variable degrees of protection against flavivirus infection in mouse and monkey disease models (see Table 1). However, there are few studies comparing immunization with NS1 in combination with envelope (E) protein, particularly with truncated envelope (E) protein.

A substantial amount of NS1 is displayed on the surface of virally-infected cells (Smith, G. W., and P. J. Wright. 1985. Synthesis of Proteins and Glycoproteins in Dengue Type 2 Virus-Infected Vero and Aedes Albopictus Cells. *J. Gen. Virol.* 66: 559-71) and immunoprophylaxis appears to be due to T-lymphocyte killing (e.g. Hall, R. A., T. N. H. Brand, M. Lobigs, M. Y. Sangster, M. J. Howard, and J. S. Mackenzie. 1996. Protective Immune Responses to the E and NS1 Proteins of Murray Valley Encephalitis Virus in Hybrids of Flavivirus-Resistant Mice. *J. Gen. Virol.* 77: 1287–94 Jacobs, S. C., J. R. Stephenson and G. W. G. Wilkinson. 1994. Protection Elicited by Replication-Defective Adenovirus Vector and Aedes Albopictus Cells. *J. Gen, Virol* 66: 559-71 ) and/or complement-mediated cytolysis (Schlesinger, J. J., M. W. Brandriss, J. R. Putnak, and E. E. Walsh. 1990. Cell Surface Expression of Yellow Fever Virus Non-structural Glycoprotein NS1: Consequences of Interaction with Antibody. *J. Gen. Virol.* 71: 593–99 Schlesinger, J. J., M. Foltzer, and S. Chapman. 1993. The Fc Portion of Antibody to Yellow Fever Virus NS1 is a Determinant of Protection against YF Encephalitis in Mice. *Virol.* 192: 132–141 Lin, Y.-L., L.-K. Chen, C.-L. Liao, C.-T. Yeh, S.-H. Ma, J.-L. Chen, Y.-L. Huang, S.-S. Chen and H.-Y. Chiang. 1998. DNA Immunization with Japanese Encephalitis Virus Nonstructural Protein NS1 Elicits Protective Immunity in Mice. *J. Virol.* 72: 191–200) facilitated by NS1-reactive antibodies. In some cases at least, it appears that poor protection is associated with rapidly replicating flaviviruses and may be due to a relatively short window of opportunity for destruction of infected cells prior to virion release. For example, Falgout, B., R. Chanock, and C. -J. Lai. 1989. Proper Processing of Dengue Virus Nonstructural Glycoprotein NS1 Requires the N-Terminal Hydrophobic Signal Sequence and the Downstream Nonstructural Protein NS2a. *J. Virol.* 63: 1852–60) were unable to get good protection against DEN-4 despite using a immunization protocol and antigen preparation analogous to that giving complete protection against DEN-2; they attribute this to the slower replication rate of the latter. Also Cane, P. A., and E. A. Gould. 1988. Reduction of Yellow Fever Virus Mouse Neurovirulence by Immunization with a Bacterially Synthesized Non-structural Protein (NS1) Fragment. *J. Gen. Viro.* 69: 1241–46 were able to obtain significant protection against a slow growing strain, but not more virulent strains of Yellow Fever (YF), following immunization with *E. coli*-expressed YF NS1. However, mouse strain and gender also seem to be important, as Qu, X., W. Chen, T. Maguire, and F. Austin. 1993. Immunoreactivity and Protective Effects in Mice of a Recombinant Dengue 2 Tonga Virus NS1 Protein Produced in a Baculovirus Expression System. *J. Gen. Virol.* 74: 89–97were able to get reasonable protection against DEN-2 in BALB/c and, to a lesser degree, randomly bred females, but no protection was obtained with males of either strain or either gender of inbred strain $CBA/T_6T_6$.

It is interesting to note that DNA vaccination of mice with a construct designed to express JEV NS1 provided a higher level of protection (90% vs. 70%) than obtained with an analogous construct directing expression of prM and E proteins (Lin et al., '9 supra). Clearly different mechanisms mediate the immunoprophylactic activities of viral structural and nonstructural proteins and perhaps DNA vaccination is better suited to the latter. Alternatively, the NS1 construct may simply provide more efficient antigen expression and/or secretion than the prME DNA vaccine.

TABLE 1

| Immunogen | Protection Results | Reference |
|---|---|---|
| NS1 immunoaffinity purified from tissue culture cells infected with Yellow Fever 17D virus. | Monkey challenge: lethal subcutaneous dose of Yellow Fever African strain Dakar 1279 virus.<br>Protection: 4 of 5 NS1-immunized animals survived vs. 0 of 4 for the mock-immunized control. | Schlesinger et al, '86* |
| NS1 immunoaffinity purified from tissue culture cells infected with Yellow Fever 17D virus | Mouse challenge: intracerebral injection of Yellow Fever 17D virus.<br>Protection: all 11 NS1-immunized mice survived vs. 2 of 10 control mice mock-immunized with ovalbumin. | Schlesinger et al, '85** |
| *E. coli* expressed Yellow Fever 17D NS1-β-galactosidase fusion; produced as inclusion bodies which were partially purified and directly mixed with adjuvant. | Mouse challenge: intracerebral injection of Yellow Fever 17D RMP virus.<br>Protection[a]: 42 out of 50 mice survived vs. 32/50 for the control group mock-immunized with β-gal. | Cane and Gould, '88 supra |
| Recombinant vaccinia virus expressing Yellow Fever 17D NS1-NS2A-NS2B (which is processed to yield native-like NS1) | Mouse challenge: intracerebral injection of Yellow Fever 17D virus.<br>Protection: 17 of 31 NS1-immunized mice were protected, while none of the control group, mock-immunized with wild type vaccinia virus survived. | Putnak and Schlesinger, '90 supra |
| Recombinant vaccinia virus expressing Murray Valley encephalitis (MVE) NS1-NS2A (which is processed to yield native-like NS1) | Mouse challenge: intracerebral injection of MVE virus.<br>Protection: 9 of 19 NS1-immunized mice were protected, while only 1/18 BSA-immunized animals survived. | Hall et al, '96 supra |
| NS1 purified from tissue culture cells infected with Murray Valley encephalitis (MVE) virus. | Mouse challenge: intracerebral injection of MVE virus.<br>Protection: 17 of 20 mice were protected vs. 1/18 for control group. | Hall et al, '96 supra |
| Baculovirus expressed Japanese Encephalitis Virus (JEV) NS1, crude cell lysate (note that proper processing at the NS1-NS2A junction did not occur and consequently NS1 did not form the native-like homodimer) | Mouse challenge: intraperitoneal injection of JEV.<br>Protection[a]: not significantly better than negative control group, however average survival time was slightly longer with the NS1-immunized group. | McCown et al, '90 infra |
| Recombinant vaccinia virus expressing JEV NS1-NS2A (processed to yield native-like NS1) | Mouse challenge: intraperitoneal injection of JEV (strain P3).<br>Protection: 11 out of 20 immunized mice vs. none of 10 control mice mock-immunized with the parental vaccinia vector containing no JEV sequences. | Konishi et al, '91 infra |
| Naked DNA vaccine encoding JEV NS1; three doses injected intramuscularly | Mouse challenge: intraperitoneal injection of 10 × $LD_{50}$ of JEV (strain RP-9).<br>Protection: 9 of 10 survived vs. 4 of 10 injected with the plasmid vector not carrying a viral DNA insert. | Lin et al., '98 supra |
| NS1 immunoaffinity purified from tissue culture cells infected with DEN-2 virus | Mouse challenge: intracerebral injection of DEN-2 and DEN-1 (neurovirulent Hawaii strain) viruses.<br>Protection: (DEN-2 chall.) 29 of 33 NS1-immunized mice survived vs. 20/34 for control group mock-immunized with ovalbumin. However no protection from DEN-1 challenge was obtained. | Schlesinger et al, '87‡ |
| NS1 purified from tissue culture cells infected with DEN-2 virus via conventional chromatography. | Mouse challenge: intracerebral injection of DEN-2 virus.<br>Protection: None. | Feighny et al, '92 infra |
| Baculovirus expressed DEN-2 NS1-NS2A (naturally processed to native-like NS1), crude cell lysate. | Mouse challenge: intracerebral injection of DEN-2 virus.<br>Protection[b]: all 5 NS1-immunized mice survived vs. 5 of 9 mice mock-immunized with negative control cell lysates. | Qu et al, '93 supra |
| Recombinant vaccinia virus expressing DEN-2 NS1-NS2A (processed to yield native-like NS1) | Mouse challenge: intracerebral injection with DEN-2 virus.<br>Protection: 12 of 24 NS1-immunized mice survived vs. none of 20 control animals mock-immunized with parental vaccinia vector. | Falgout et al, '90 supra |

TABLE 1-continued

| Immunogen | Protection Results | Reference |
|---|---|---|
| Recombinant vaccinia virus expressing DEN-4 NS1-NS2A (processed to yield native-like NS1) | Mouse challenge: intracerebral injection with DEN-4 virus. Protection: all 28 NS1-immunized mice survived vs. 8 of 52 for control. | Falgout et al., '90 supra |

[a]protection levels seen in these studies may have been reduced by the non-native conformation of NS1.
[b]these results were quite dependent on mouse strain and gender, see text for details.
*Schlesinger, J. J., M. W. Brandriss, C. B. Cropp, and T. P. Monath, 1986. Protection against Yellow Fever in Monkeys by Immunization with Yellow Fever Virus Nonstructural Protein NS1. J. Virol. 60; 1153–55
**Schlesinger, J. J., M. W. Brandriss, and E. E. Walsh, 1985. Protection against 17D Yellow Fever Encephalitis in Mice by Passive Transfer of Monoclonal Antibodies to the Nonstructural Glycoprotein gp48 and by Active Immunization with gp48, J. Immunol 135: 2805–09.

Schlesinger, J. J., M. W. Brandriss, C. B. Cropp, and T. P. Monath. 1986. Protection against Yellow Fever in Monkeys by Immunization with Yellow Fever Virus Nonstructural Protein NS1. *J. Virol.* 60: 1153–55—and on next line, please insert—** Schlesinger, J. J., M. W. Brandriss, and E. E. Walsh. 1985. Protection against 17D Yellow Fever Encephalitis in Mice by Passive Transfer of Monoclonal Antibodies to the Nonstructural Glycoprotein gp48 and by Active Immunization with gp48. *J. Immunol.* 135: 2805-09.

Despite uncertainty regarding the exact mechanism of NS1-mediated immunoprophylaxis against flavivirus infection, it is clearly different from the virus neutralizing activity provided by α-envelope antibodies since little of the NS1 protein is present on the viral surface. It is reasonable, therefore, to suspect that NS1 may augment effectiveness of flavivirus vaccines based on recombinant viral E protein by providing a second route of protection to that afforded by an immunological response against E protein. However, there have been relatively few studies that directly compare the protective properties of immunogens composed of flavivirus envelope protein in isolation versus in combination with NS1. McCown, Jack, Mark Cochran, Robert Putnak, Robert Feighny, Jeanne Burrous, Erik Henchal, and Charles Hoke. 1990. Protection of Mice Against Lethal Japanese Encephalitis with a Recombinant Baculovirus Vaccine. *Am. J. Trop. Med Hygiene.* 42 (No. 5): 491–499) tested crude cell lysate Schlesinger, J. J., M. W. Brandriss, and E. E. Walsh. 1987. Protection of Mice against Dengue 2 Virus Encephalitis by Immunization with the Dengue 2 Virus Non-structural Glycoprotein NS1. *J. Gen. Virol.* 68: 853–57 immunogens prepared from baculovirus constructs based on JEV E or NS1 individually as well as a polyprotein containing prM/M, E, NS1 and NS2a/b. Fifteen of twenty mice immunized with E were protected from a subsequent intraperitoneal challenge of JEV, while protection was 13/19 in the case of prM-NS2 polyprotein; the lack of improvement in protection by including NS1 is perhaps not surprising since immunization with this protein alone afforded no protection in this study. A similar study done in monkeys yielded some protection against DEN-4 viremia following immunization with a crude lysate from insect cells infected with a baculovirus DEN-4 C-prM-E-NS1-NS2a polyprotein construct, but parallel immunization with baculovirus-expressed E gave a similar level of protection (E alone: no viremia in 1 of 3 animals; C-NS2a polyprotein: 1 of 6 showed no viral growth, while another had viremia of reduced duration. Lai, C.-J., Y.-M. Zhang, R. Men, M. Bray, R. M. Chanock, D. R. Dubois, and K. H. Eckels. 1990. Immunization of Monkeys with Baculovirus Recombinant-Expressed Dengue Envelope and NS1 Glycoproteins Induces Partial Resistance to Challenge with Homotypic Dengue Virus. In *Vaccines* 90, edited by F. Brown, R. M. Chanock, H. S. Ginsberg and R. A. Lerner. Cold Spring Harbor: Cold Spring Harbor Laboratory Press. Two other studies of mouse protection provided by E vs. E+NS1 immunizations, were done under conditions that yielded complete protection with E alone and thus allowed little opportunity for augmentation by NS1 (JEV vaccinia prM-E vs. prM-NS2a: Konishi, E., S. Pincus, B. Fonseca, R. Shope, E. Paoletti, and P. Mason. 1990. Comparison of Protective Immunity Elicited by Recombinant Vaccinia Viruses that Synthesize E or NS1 of Japanese Encephalitis Virus. *Virology* 185: 401–410; DBN-4 vaccinia C-B vs. C-NS2a: Bray, M,, B. Zhao, L. Markoff, K. H. Eckels, R. M. Chanock, and C.-J. Lai. 1989. Mice Immunized with Recombinant Vaccinia Virus Expressing Dengue 4 Virus Structural Proteins with or without Nonstructural Protein NS1 are Protected against Fatal Dengue Virus Encephalitis. *J. Virol.* 63: 2853–56), although it appears that the level of protection observed may be largely dependent upon parameters of the animal model used. The art contains few clear examples of controlled comparisons between use of truncated envelope protein alone and in combination with nonstructural protein, NS1, to stimulate a protective response. The studies of McCown et al. ('90) and Feighny, Robert, Jeanne Burrous, Jack McCown, Charles Hoke, and Robert Putnak. 1992. Purification of Native Dengue-2 Viral Proteins and the Ability of Purified Proteins to Protect Mice. *Am. J. Trop. Med Hygiene* 47 (No. 4): 405–412) in fact suggest that NS1 affords no protection.

DISCLOSURE OF THE INVENTION

The invention provides immunogenic compositions containing, as an active ingredient, a secreted recombinantly produced nonstructural (NS) protein of a Flavivirus. The invention further provides immunogenic compositions containing as a second active ingredient, a secreted recombinantly produced Flavivirus truncated envelope protein (E). These immunogenic compositions are capable of eliciting the production of neutralizing antibodies against a Flavivirus. In the illustrations below, the nonstructural protein NS1 from dengue virus, a Flavivirus, is recombinantly expressed and secreted from Drosophila host cells. Similarly expressed is the truncated envelope protein (E). Together, NS1 and E serve to protect mice challenged with infection by dengue virus.

One aspect of the present invention is drawn to methods of the recombinant expression and secretion from eucaryotic host cells of nonstructural (NS) protein subunits of Flavivirus. One embodiment of this invention relates to the methods of recombinant expression and secretion from Drosophila host cells of the NS1 protein of Flavivirus. Further, this invention contemplates methods of the recombinant expression and secretion of other nonstructural proteins of Flavivirus using other vectors, control sequences, secretory signal sequences as well as other eucaryotic host cells.

Another aspect of the present invention relates to the use of compositions of a Flavivirus truncated envelope (E) protein in combination with nonstructural proteins of Flavivirus, as immunogenic antigens that stimulate an immunological response in a host subject animal, inter alia, by stimulating antibody formation and/or a cellular immune response. One embodiment of this invention includes an immunogenic composition of matter comprising the Flavivirus truncated envelope (E) protein, 80%E, and the Flavivirus nonstructural (NS) protein, NS1.

Other aspects of this invention include: use of a therapeutically effective amount of the immunogenic composition in an acceptable carrier as a vaccine; a therapeutically effective amount of the immunogenic composition in an acceptable carrier as a pharmaceutical composition; and use of the immunogenic composition as an immunodiagnostic for the detection of a Flavivirus. The invention envisions such immunodiagnostics as using the immunogenic composition as an antigen as well as immunodiagnostics employing antibodies elicited in response to the immunogenic composition.

Still other aspects of this invention include the compositions of nonstructural proteins of Flavivirus. These compositions, including NS1, are useful as immunodiagnostics for the detection of Flavivirus. Such immunodiagnostics include nonstructural proteins or fragments thereof as immunogenic compositions as well as immunodiagnostics employing antibodies elicited in response to the immunogenic compositions.

The following is a more detailed description of the present invention. The invention provides, for the first time, a means for increasing the protection of a subject against infection by a Flavivirus, by including in a vaccine an immunogenic composition that contains a recombinantly expressed Flavivirus nonstructural (NS) protein subunit secreted from a eucaryotic host cell. The DNA sequence encoding a nonstructural (NS) protein is obtained from a Flavivirus, and expressed following the functional and operable insertion of the DNA sequence into an expression vector containing control sequences and secretory signal sequences.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, Molecular Cloning: A Laboratory Manual, Second Edition (1989), Oligonucleotide Synthesis (M. J. Gait Ed., 1984), Animal Cell Culture (R. I. Freshhey, Ed., 1987), the series Methods in Enzymology (Academic Press, Inc.); Gene Transfer Vectors for Mammalian Cells (J. M. Miller and M. P. Calos eds. 1987), Handbook of Experimental Immunology, (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

For example, Flavivirus nonstructural (NS) proteins may include: NS1, NS2a, NS2b, NS3, NS4a, NS4b and NS5 (Chambers et al, '90 supra; Henchal and Putnak, '90 supra). These DNA sequences encoding nonstructural protein sequences may be operably linked to control sequences that direct genetic expression of said nonstructural protein sequences. A further contemplated embodiment includes the use of control sequences such as the metallothionein promoter functional in Drosophila host cells.

Such methods contemplated by this invention include a method of expressing a Flavivirus nonstructural (NS) protein, comprising, transforming a eucaryotic host cell with a recombinant vector comprising a DNA sequence encoding a Flavivirus nonstructural (NS) protein; cultivating the transformed host under permissive conditions for expression and secretion of the nonstructural protein (NS); and isolating the secreted nonstructural (NS) protein.

A more specific embodiment of this invention relates to the recombinant expression and secretion from Drosophila host cells of the NS1 protein of Flavivirus. Further, this invention contemplates the recombinant expression and secretion of other nonstructural proteins of Flavivirus using other vectors, control elements, signal or secretion elements as well as other eucaryotic host cells.

The recombinantly expressed and secreted NS proteins may be purified using a variety of means, including, but not limited to: conventional chromatography; immunoaffinity chromatography; and other techniques recognized in the art. The molecular weight of purified NS proteins may similarly be determined using technologies found in the art, such as polyacrylamide gel electrophoresis; size exclusion chromatography; density gradient centrifugation.

Another embodiment of the present invention relates to the use of compositions of a Flavivirus truncated envelope (E) protein in combination with nonstructural proteins of Flavivirus; as immunogenic antigens that stimulate an immunological response in a host subject, inter alia, by eliciting antibody formation and/or a cellular immune response. A more specific embodiment of this invention includes an immunogenic composition of matter comprising the Flavivirus truncated envelope (E) protein, 80%E, and the Flavivirus nonstructural (NS) protein, NS1. The recombinant product we have focused most of our efforts on is a soluble form of flaviviral E, which is truncated at the carboxy-terminal end resulting in a polypeptide which represents approximately 80% of the full-length E molecule (amino acids 1–395; 80%E).

The recombinant expression and secretion of Flavivirus truncated envelope (E) protein was carried out. The construction of recombinantly expressed Flavivirus truncated envelope (E) protein secreted from eucaryotic host cells has been thoroughly presented in copending patent application by Peters et al., Ser. No. 08/904,227, which is hereby incorporated in its entirety by reference herein.

The full-length NS1 gene was obtained from PCR amplification of a sequence from DEN-2 PR159/S1 cDNA clone #2 (Hahn, Young S., Ricardo Galler, Tim Hunkapiller, Joel M. Dalrymple, James H. Strauss, and Ellen G. Strauss. 1988. Nucleotide Sequence of Dengue 2 RNA and Comparison of the Encoded Proteins with Those of Other Flaviviruses. *Virology* 162: 167–180; pYH2, provided by J. R. Putnak, Walter Reed Army Institute of Research) using primers designed to add flanking restriction endonuclease sites as well as two consecutive stop codons immediately following the coding region (see FIG. 1). The construction of recombinant expression and secretion vectors provides that the sequences encoding the proteins to be expressed are operably linked to control sequences and secretory signal sequences. The truncated E protein may be expressed separately or fused to NS1.

"Operably linked" refers to a juxtaposition wherein the components are configured so as to perform their usual function. Thus, control sequences operably linked to coding sequences are capable of effecting the expression of the coding sequence. "Control sequence" refers to a DNA sequence or sequences which are capable, when properly ligated to a desired coding sequence, of effecting its expression in hosts compatible with such sequences. Such control sequences include in eucaryotic hosts, promoters and termination signals. Additional factors necessary or helpful in effecting expression may subsequently be identified. As used herein, "control sequences" simply refers to whatever DNA sequence may be required to effect expression in the particular host used.

"Secretory signal sequence" refers to a peptide sequence, encoded by a DNA sequence or sequences, which are capable when the DNA sequence or sequences are properly ligated to a desired coding sequence, of effecting secretion of the polypeptide from hosts compatible with such sequences. The ftnction of the signal peptide encoded by the DNA sequence is thought to be important for targeting the synthesized polypeptide for secretion. A signal sequence plays an important role in ensuring the proper localization of a newly synthesized protein. Generally they provide "topogenic signals" (Blobel, G. Proc. Nat. Acad. Sci., U.S.A. 77, 1496–1500 (1980), which target the attached protein sequence to various destinations within or external to the cell. This is particularly important for secreted proteins whose target sites are extracellular. It is also helpful for recombinant protein production as it can be easier to purify an expressed protein from the extracellular media rather than having to lyse the cells and purify from a whole cell extract.

"Cells" or "recombinant host cells", "eucaryotic host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used. It is also, of course, possible to express genes encoding polypeptides in eucaryotic host cell cultures derived from multicellular organisms. See, Examples 1–7, infra; and for example, Axel, et al., U.S. Pat. No. 4,399,216 which is hereby incorporated by reference herein. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., Nature (1978) 273:113), or other viral promoters such as those derived from polyoma, Adenovirus 2, bovine papilloma virus, or avian sarcoma viruses. The controllable promoter, hMT-II (Karin, M., et al., Nature (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. A wide variety of eucaryotic hosts are also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth. Commonly used eucaryotic systems include yeast, insect cells, mammalian cells, avian cells, and cells of higher plants. The list is not exhaustive. Suitable promoters are available that are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions. The particulars for the construction of expression systems suitable for desired hosts are known to those in the art. For recombinant production of the protein, the DNA encoding it is suitably ligated into the expression system of choice, and the system is then transformed into the compatible host which is then cultured and maintained under conditions wherein expression of the foreign gene takes place.

Depending on the host cell used, transformation is done using standard techniques appropriate to such cells. The calcium treatment employing calcium chloride, as described by Cohen, S. N., Proc Natl Acad Sci (USA) (1972) 69:2110, or the RbC12 method described in Maniatis, T., et al., Molecular Cloning: A Laboratory Manual (1982) Cold Spring Harbor Press, p. 254 may be used for procaryotes or other cells that contain substantial cell wall barriers. For mammalian cells without such cell walls, the calcium phosphate precipitation method of Graham and van der Eb, Virology (1978) 52:546, optionally as modified by Wigler, M., R. Sweet, G. K. Sim, B. Wold, A. Pellicer, E. Lacey, T. Maniatis, S. Silverstein, and R. Axel. 1979. Transformation of Mammalian Cells with Genes from Procaryotes and Eucaryotes. *Cell* 16: 777–785) may be used. Transformations into yeast may be carried out according to the method of Van Solingen, P., et al., J Bact (1977) 130:946 or of Hsiao, C. L., et al., Proc Natl Acad Sci (USA) (1979) 76:3829.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired. Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution: in the examples herein, typically, an excess of restriction enzyme is used to ensure complete digestion of the DNA substrate. Incubation times of about one to two hours at about 37° C. are workable, although variations can be tolerated. After each incubation, protein is removed by extraction with phenol/chloroform or heat inactivated, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology (1980) 65:499–560. Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20 to 25° C. in 50 mM Tris pH 7.6, 50 mM NaCl, 6 mM $MgCl_2$, 6 mM DTT and 5–10 $\mu$M dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenollchloroform and ethanol precipitated. Treatment under appropriate conditions with SI nuclease or Bal-3 1 results in hydrolysis of any single-stranded portion.

Immunogenic compositions containing Flavivirus non-structural (NS) proteins or truncated envelope (E) proteins to be used as antigens are prepared and utilized in ways that the skilled artisan would readily recognize. Antigens can be used in immunoassays to detect antibody levels (or conversely antibodies can be used to detect antigen levels) and correlation can be made with disease. Immunoassays based on well defined, recombinant antigens can be developed to replace the invasive diagnostics methods that are used today. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays that utilize biotin and avidin, and enzyme-labeled and mediated immunoassays, such as ELISA assays. Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Vaccines may either be prophylactic (to prevent infection) or therapeutic (to treat disease after infection). Such vaccines comprise antigen or antigens, usually in combination with "pharmaceutically acceptable carriers" or "acceptable carriers", as may used interchangeably as will be clear from the context, which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a toxoid, such as a toxoid from diphtheria, tetanus, cholera, *H. pylori,* etc. Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L 121, and thr-MDP (see below) either microfluidized into a submicron emulsion or vortexed to generate a larger particle size emulsion, and (c) Ribi TM adjuvant system (RAS), (Ribi Immunochem, Hamilton, Mont.) containing 2% Squalene, 0.2% Tween 80, and one or more bacterial cell wall components from the group consisting of monophosphorolipid A (MPL), trehalose dimycolate (TDM), and cell wall skeleton (CWS), preferably MPL+CWS (Detox™); (3) saponin adjuvants, such as Stimulon TM (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred. As mentioned above, muramyl peptides include, but are not limited to, N-acetyl-muramyl-L-threonyl-D-isoglutamine (thr-MDP), N-acetyl-nornuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTPPE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles. Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers. Immunogenic compositions of the present invention elicit formation of antibodies with high binding specificity to a composition of a Flavivirus truncated envelope (E) protein in combination with nonstructural proteins of Flavivirus, and more specifically antibodies with high binding specificity to a composition of a Flavivirus 80%E and NS1. Such immunogenic compositions used as vaccines comprise an immunologically effective amount of the antigenic polypeptides, as well as any other of the above-mentioned components, as needed. By "immunologically effective amount", or "therapeutically effective amount" as may used interchangeably and as will be clear from the context, it is meant that the administration of that amount to an individual or host subject animal, either in a single dose or as part of a series, is effective for treatment or prevention. This amount varies depending upon the health and physical condition of the individual or host subject animal to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

BRIEF DESCRIPTION OF THE DRAWINGS

FIG. 1 shows the PCR primers used to clone NS1. Upper case represents regions homologous to dengue with the reading frame indicated, adapter sequences are in lower case. The first capitalized codon of 0.2422 p codes for $Asp_1$ of NS1; the endpoint specified by 0.3477 m differs from that identified by Hahn et al '88 supra; (nucleotide 3660), but is in agreement with the 3' termini identified for multiple other flaviviruses (reviewed in Chambers et al, '90, supra).

MODES OF CARRYING OUR THE INVENTION

The following examples are intended to illustrate but not to limit the invention.

EXAMPLE 1

Construction of Expression Vector for NS1 Secretion from Drosophila Cells

The NS1 gene used for the invention is from DEN-2 strain PR159/S1; this is a small-plaque, temperature-sensitive vaccine-candidate strain (Eckels, K. H., V. R. Haarrison, P. L. Summers, and P. K. Russell. 1980. Dengue-2 Vaccine: Preparation from a Small-Plaque Virus Clone. *Infect. Immun.* 27: 175–180) that is identical to the wild type parent, PR159 throughout the NS1 coding region (our unpublished data combined with that of Hahn et al, '88 supra ). Initially, the full-length NS1 gene was PCR amplified from DEN-2 PR159/S1 cDNA clone #2 (Hahn et al, '88 supra; pYH2, provided by J. R. Putnak, Walter Reed Army Institute of Research) using primers designed to add flanking restriction endonuclease sites as well as two consecutive stop codons immediately following the coding region (see FIG. 1). The amplified product was digested with XbaI and cloned into similarly cut pUC 19 vector. DNA sequencing of the recombinant p29D2NS1.2, confirmed that no mutations had been introduced during PCR amplification and cloning.

Figure 2:
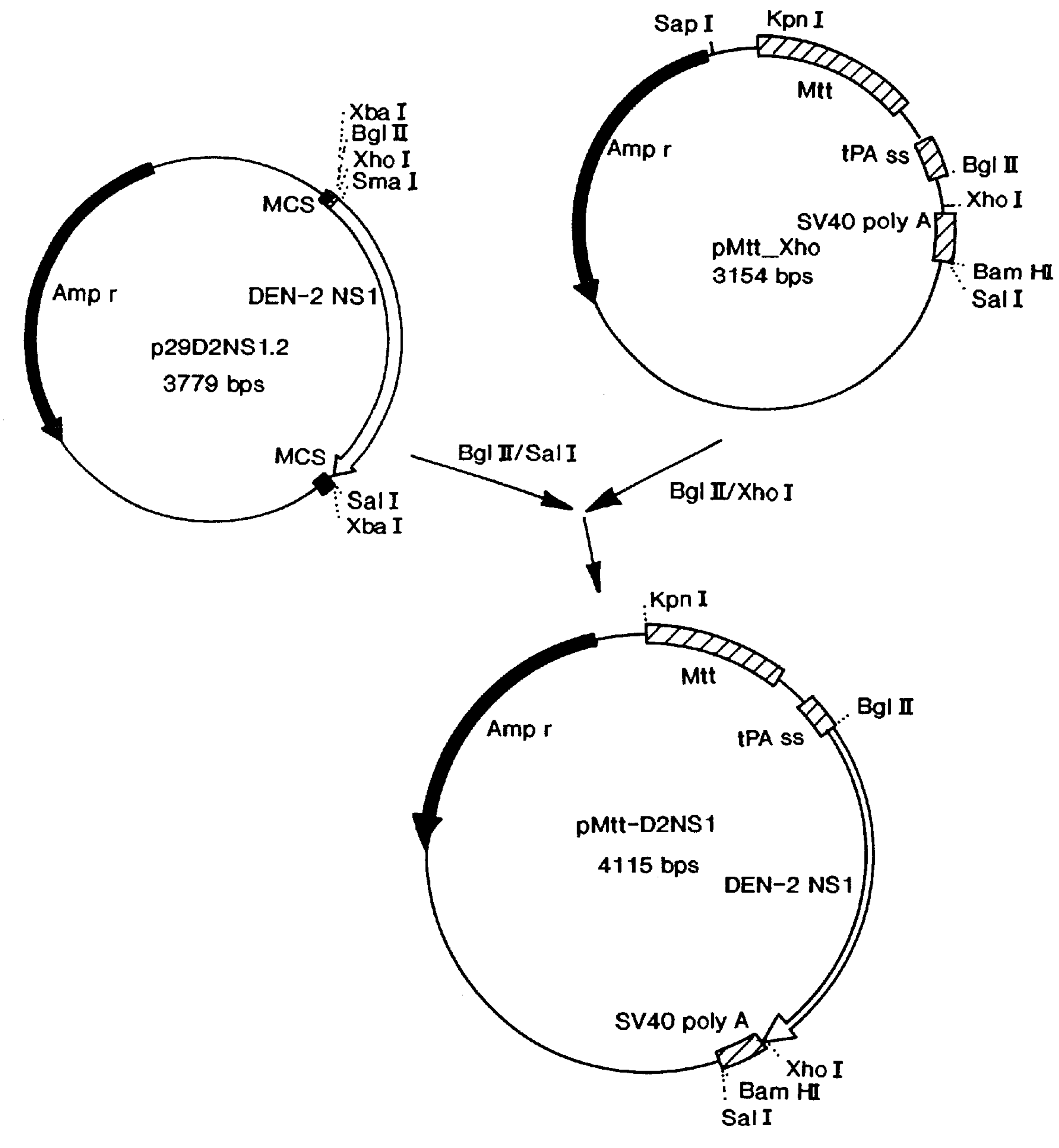
FIG. 2 shows the construction of pMtt-D2NS1
Figure 3:
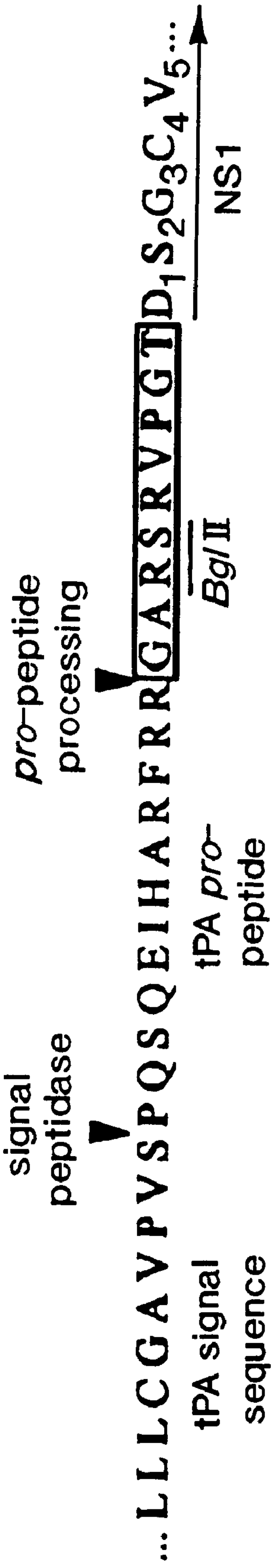
FIG. 3 shows the amino acid sequence of the primary translation product. The predicted amino acid sequence is in single letter code with the expected proteolytic processing sites indicated. The boxed region represents extraneous residues of the secreted recombinant NS1 and amino acid numbering is that of natural NS1.

To facilitate insertion of the NS1 coding sequence, one of the two XhoI sites contained within the *Drosophila melanogaster* expression vector pMttbns (SmithKline Beecham) was removed by excising a 19 base pair BamHI fragment which contains the XhoI site at position 885. The resulting pMtt-Xho expression plasmid was cut with BgiII and XhoI and combined with the NS1-encoding fragment liberated from p29D2NS1.2 by digestion with BglII and SalI (see FIG. 2); integrity at the splice junctions was confirmed by DNA sequencing. The recombinant, pMtt-D2NS1 contains the NS1 coding region embedded in a gene structure engineered to provide regulated extracellular expression in Drosophila cells. Transcription is driven by the strong promoter region from the Drosophila metallothionein gene and thus is switched off in the absence of metal ion inducer; message polyadenylation is facilitated by the SV40 polyA signal. NS1 is targeted for secretion by fusion to the pre/pro-peptide region of tissue plasminogen activator (tPA), signal peptidase and pro-peptide processing is expected to yield full-length NS1 with a nine residue N-terminal extension (see FIG. 3).

EXAMPLE 2

NS1 Expression in *Drosophila melanogaster* S2 Cells

*Drosophila melanogaster* Schneider-2 cells (S2 ATCC, Rockville, Md.) were cotransfected with pMtt-D2NS1 plus pCoHygro selection,asmid at a weight ratio of 20:1 via the calcium phosphate coprecipitation method (Wigler, M., R. Sweet, G. K. Sim, B. Wold, A. Pellicer, E. Lacey, T. Maniatis, S. Silverstein, and R. Axel. 1979. Transformation of Mammalian Cells with Genes from Procaryotes and Eucaryotes. Cell 16: 777–785; Gibco BRL, Grand Island, N.Y.). The pCoHygro selection plasmid (van der Straten, A., H. Johansen, M. Rosenberg, and R. W. Sweet. 1989. Introduction and Constitutive Expression of Gene Products in Cultured Drosophila Cells using Hygromycin B Selection. *Meth. Mol. Cell. Biol.* 1: 1–18 SmithKline Beecham) contains the *E. coli* hygromycin B phosphotransferase gene under transcriptional control of the *D. melanogaster* copia transposable element long terminal repeat and confers resistance to hygromycin B. Transfectants were selected for outgrowth in Schneider's medium (Gibco BRL) supplemented with 10% fetal bovine serum (FBS; Hyclone) and 300 $\mu$g/ml hygromycin B (Boerhinger Mannheim). Following significant outgrowth, transfectants were plated at a cell density of $2\times10^6$ cells/ml in serum-free IPL-41 medium supplemented with lipids, yeastolate, and Pluronic F68 (Gibco BRL). Cell-free medium was harvested after 7 days of induction with 200 $\mu$M $CuSO_4$.

Figure 4:
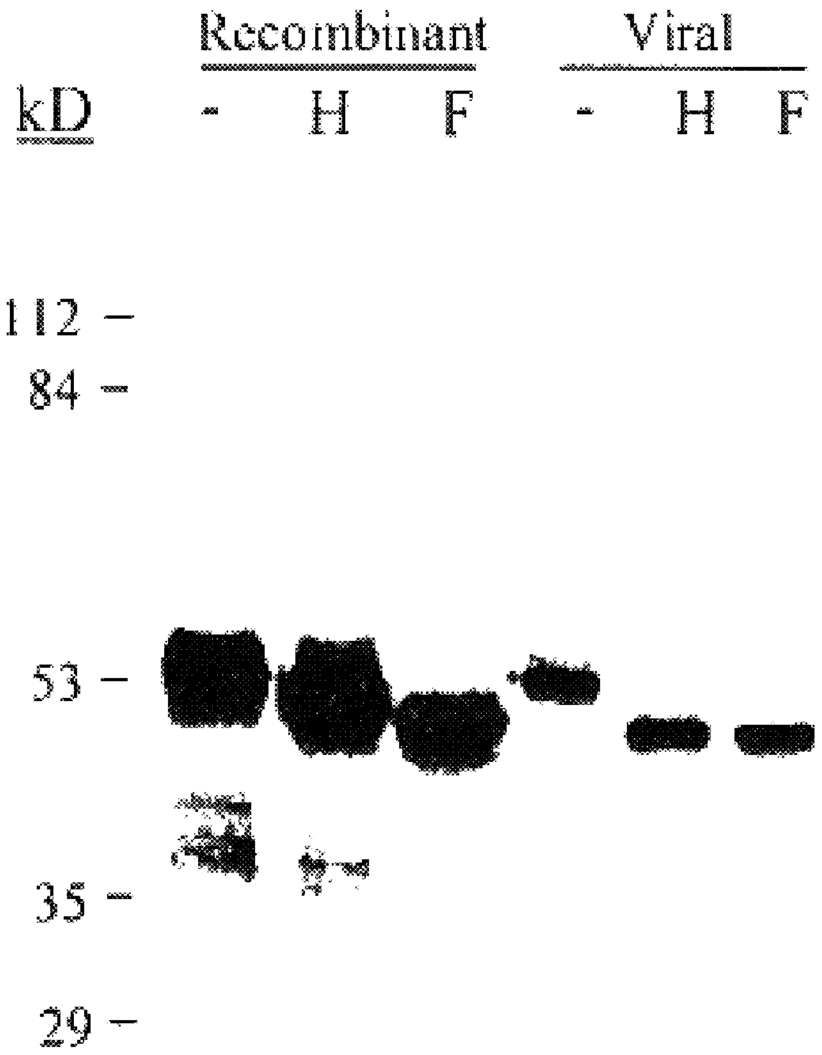
FIG. 4 is a Western blot showing the glycosylation of recombinant and viral NS1's. Western blot of S2 DEN-2 NS1 cell culture medium (Recombinant) and Dengue 2-infected $C_6$/36 cell pellets (Viral) without glycosidase digestion (–) as well as after endoglycosidase H (E) or peptide:N-glycosidase F (P).

NS1 expression was evaluated by Western blot analyses, using $\alpha$-DEN-2 hyperimmune mouse ascitic fluid (HMAF) and $\alpha$-NS1 monoclonal antibody (MAb) 7E11 (see FIG. 4). Substantial quantities of immunoreactive product of the appropriate molecular weight was detected in the culture medium, with some NS1 also observed intracellularly. Recombinant protein expression was sufficient to allow identification in Coomassie-stained SDS-PAGE gels of crude unconcentrated culture medium.

EXAMPLE 3

Glycosylation and Oligomerization of Recombinant NS1 is Native-like

Recombinant NS1 expressed in Drosophila cells and its viral cognate secreted by DEN-2 infected $C_6$/36 mosquito cells comigrate during SDS-PAGE (FIG. 4). Furthermore, digestion of viral and recombinant NS1's with the glycolytic enzyme PNGase F (peptide:N-glycosidase F) results in identical mobility shifts, indicating that these proteins are similarly glycosylated (FIG. 4). Consistent with NS1 produced by mammalian cells infected with DEN-2 (Winkler, G., V. B. Randolph, G. R. Cleaves, T. E. Ryan, and V. Stoller. 1988. Evidence that the Mature Form of the Flavivirus Nonstructural Protein NS1 is a Dimer. *Virol.* 162: 187–96), endoglycosidase H treatment of recombinant NS1 removed roughly half of the sugar, however DEN-2 NS1 produced in virally-infected $C_6$/36 insect cells was fully endoglycosidase H-sensitive. This difference between flavivirus NS1 proteins from virally-infected mammalian and mosquito cells has been observed previously (Mason, '89) and is presumably a reflection of the inability of latter to synthesize complex-type protein-linked carbohydrate (Hsieh, P., and P. W. Robbins. 1984. Regulation of Asparagine-linked Oligosaccharide Processing. *J. Biol. Chem.* 259: 2375–382).

Figure 5:
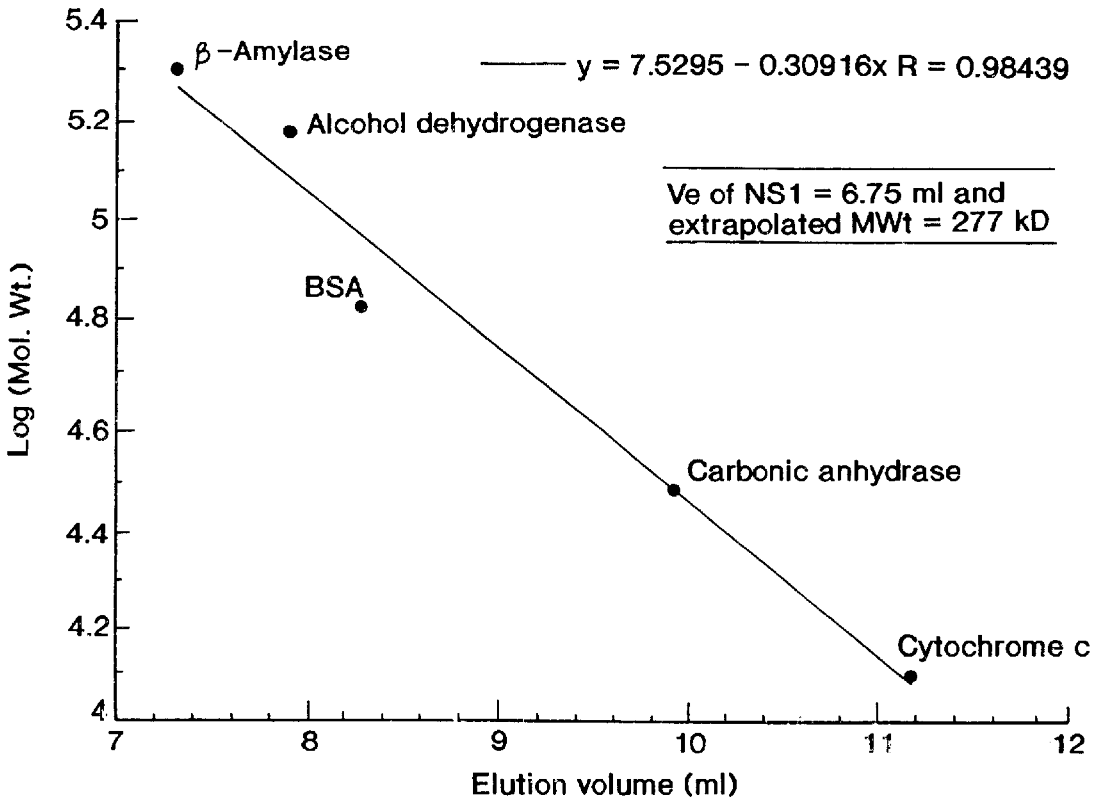
FIG. 5 is a graph depicting the size exclusion chromatographic analysis of NS1. The apparent molecular weight of NS1 was estimated by linear regression analysis of data obtained for standard proteins. Size exclusion chromatography was done using a TSK G3000 $SW_{XL}$ column (TosoHaas) on a Hewlett Packard Ti-Series 1050 HPLC run at 0.5 ml/min. with 20 mM succinate pH 6.0.
Figure 6:
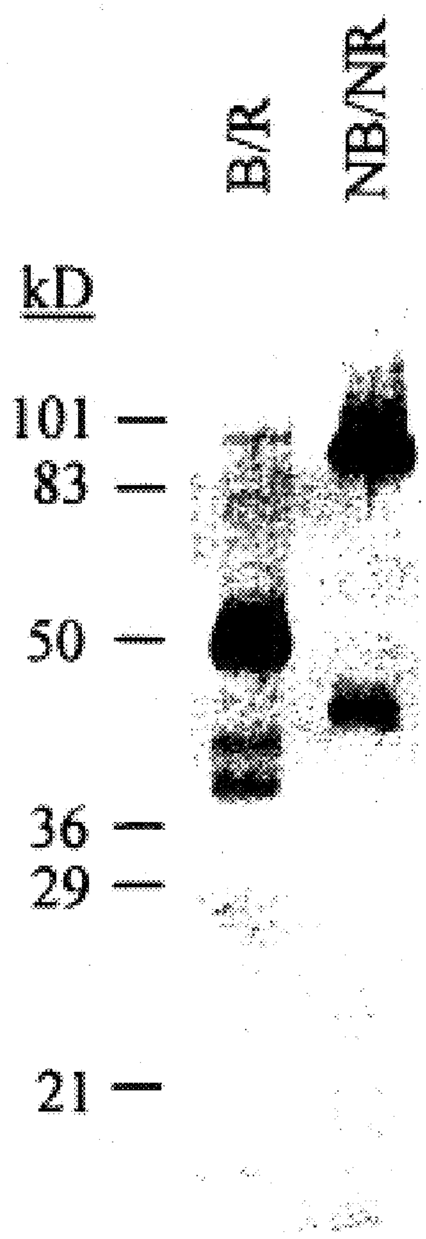
FIG. 6 is a Western blot showing the NS1 homodimer. Samples of Drosophila expressed NS1 were suspended in Laemli loading buffer with (reduced) and without (non-reducing) 100 mM dithiothreitol and then incubated at 100 or 37° C. for 5 min prior to SDS-PAGE. Electroblotted proteins were probed with anti-NS I MAb, 7E11.

Viral NS1 is an oligomeric protein; under completely native conditions its apparent molecular weight is roughly 300 kD (Crooks, A. J., J. M. Lee, L. M. Easterbrook, A. V. Timofeev, and J. R. Stephenson. 1994. The NS1 Protein of Tick-Borne Encephalitis Virus Forms Multimeric Species Upon Secretion from the Host Cell. *J. Gen. Virol.* 75: 3453–60), but in the presence of detergent it behaves as a homodimer (Crooks et al, '94 supra; Winkler et al, '88 supra). Analytical HPLC size-exclusion chromatography of recombinant NS1 confirmed that it also was oligomeric with an apparent molecular weight of ~300 kD (FIG. 5). SDS-PAGE under non-reducing conditions without sample boiling (i.e. conditions of Falconar, A. K. I., and P. R. Young. 1990. Immunoaffinity Purification of Native Dimer Forms of the Flavivirus Non-Structural Glycoprotein, NS1 *J. Virol. Meth.* 30: 325–332) demonstrated that the recombinant NS1 oligomer, like naturally occurring NS1, decomposes to a homodimer in the presence of SDS (FIG. 6).

EXAMPLE 4

Increased NS1 Expression via Cell Cloning and Bioreactor Culturing

The pMtt-D2NS1 expression vector does not contain a selectable marker and to facilitate recovery of transformants, a small amount of pCoHygro selection plasmid is included in the transfection mix. Cells acquiring hygromycin resistance through chromosomal integration of the pCoHygro plasmid will often have also incorporated pMtt-D2NS1 since separate DNA molecules are generally ligated together intracellularly prior to integration (see Kaufman, R. J. 1990. Selection and Coamplification of Heterologous Genes in Mammalian Cells. *Meth. Enzymol.* 185: 537–566). Usually however, some cell lineages recovered through hygromycin selection will not contain the cotransfection partner and furthermore the number of NS1 genes integrated per genome is likely to vary substantially. Therefore, to improve overall NS1 production, the mixed population was enriched for cell lineages that exhibit a high level of recombinant expression.

Drosophila S2 cells apparently require autocrine growth factors and grow poorly at low cell densities unless exogenous growth factors are provided. S2 DEN-2 NS1 (i.e. cells transformed with pMtt-D2NS1) subcloning was done using either preconditioned cell-free medium or a feeder layer of cells separated from the subclone seed by a membrane barrier that is porous to the growth factors, but prevents cell passage (Anopore inserts, NUNC). For the first round of enrichment, S2 DEN-2 NS1 cells were suspended in preconditioned medium (cell-free Schneider's medium used to expand Drosophila S2 cells from $2\times10^6$ to $1\times10^7$ cells/ml, mixed 1:1 with fresh medium) at a density of 20,000 cells/ml and plated at 100 $\mu$l/well in a 96-well culture dish. After outgrowth, the small-scale cultures were induced for 7 days with $CuSO_4$ (200 $\mu$M, final) and the media spotted onto a nitrocellulose membrane. Relative levels of NS1 expression were compared by immunoprobing the dot-blot with $\alpha$-NS 1 MAb 7E11 and the best expressers expanded for careful comparison at matched cell densities. Expression levels in these controlled cultures were assessed by 7E11 Western blots and Coomassie-stained SDS-PAGE gels while the percentage of NS1-expressing cells was estimated by immunofluorescence microscopy. One subclone was selected for further screening at 33 cells/well in IPL-41 medium (supplemented with lipid, yeastolate, pluronic F-68 and 10% fetal bovine serum) with autocrine growth factors provided by $10^3$ S2 DEN-2 NS1 cells per Anopore insert. Once the feeder cells reach confluency, the insert was removed and outgrowth continued. Screening was conducted as above and the best expresser subjected to two more rounds of subcloning and screening, this time at 1 cell per well. The final subelone exhibited NS1 expression levels 10 to 15-fold higher than the original mixed population.

We have also found that the level of NS1 expression can be improved an additional 3 to 4-fold by replacing conventional tissue culture methods with large-scale growth in a Bioflo 3000 bioreactor (New Brunswick Scientific). Bioreactor culturing was done using 3–4 liters of IPL-41 (Gibco BRL) medium supplemented with yeastolate (Gibco BRL; 3.33 g/l, final), lipid concentrate (Gibco BRL; 1% (v/v) final) and pluronic polyol F-68 (Gibco BRL; 0.1% (w/v) final) in a 5 liter vessel. Agitation rate was 80 rpm with two marine blade impellers and sparging with air, $O_2$, $N_2$ and $CO_2$ gases was at a rate of 133 ml/min/liter medium. pH was maintained at 6.2 using bicarbonate buffer with continuous automatic adjustment through addition of $CO_2$ and NaOH; dissolved oxygen was maintained at 50% air saturation. Cell densities at inoculation, CuSO4 (200 $\mu$M, final) induction and harvest were $1\times10^6$, $2–3\times10^6$ and $1\times10^7$ respectively.

EXAMPLE 5

Purification of Recombinant NS1 by Conventional Chromatography

Cell-free culture medium from bioreactor growth of S2 DEN-2 NS1 Drosophila cells was concentrated 13-fold by tangential-flow ultrafiltration (Minitan 30 kD MWCO, Millipore) in preparation for chromatography. The initial stage of NS1 isolation exploits its large oligomeric state (see Example 3) to facilitate partial purification via size-exclusion chromatography (SEC) on Sephacryl S200HR (Pharmacia). Typically 25 mls of crude medium concentrate was loaded onto a 2.5x45 cm column and fractionated using 20 mM sodium phosphate (pH 7.6) at a flow rate of 1.5 ml/min. NS1 elutes in the void peak and thus can be loaded in a large volume with little sacrifice in resolution; in our hands, a 2 to 3-fold increase in purity was achieved with a product yield of ~65%. Pooled SEC material is diluted 1:1 with phosphate running buffer and subject to anmmonium sulfate fractionation. Cuts done at 30, 35, 40 and 45% ammonium sulfate saturation removed contaminants, including a milky lipid-like substance that floated to the surface during centrifugation. NS1 was precipitated by addition of ammonium sulfate to 95% of saturation; this step improved purity to about 85% with a yield of ~55%.

SDS-PAGE under non-reducing conditions without sample boiling confirmed that NS1 purified in this way completely retained the detergent-resistant dimer and furthermore, its apparent molecular weight by analytical size exclusion chromatography was ~300 kD, consistent with the behavior of natural NS1 (data not shown).

EXAMPLE 6

Immunoaffinity Purification of Recombinant NS1

Immunoaffinity chromatography (IAC) was facilitated by using the α-NS1 MAb 7E11 covalently coupled to NHS-activated HiTrap resin (Pharmacia). Six mg of 7E11 purified by protein A affinity chromatography was immobilized on a 1 ml column. Fifty ml of cell-free medium from bioreactor culture of S2 DEN-2 NS1 cells was directly applied to the column and unbound material washed out with phosphate-buffered saline until eluate $OD_{280}$ returned to baseline. Bound NS1 was eluted in 100 mM glycine, pH 2.5 with immediate neutralization by adding 1.5–2 ml of 1 M phosphate pH 7.4. Product purity was estimated at ~95% by SDS-PAGE, while spectrometric methods indicated that the yield was roughly 200 μg per run. Gel electrophoresis under non-reducing conditions without sample boiling demonstrated that 80–90% of the IAC-purified product retained the detergent-resistant dimer (data not shown).

The α-NS1 MAb 7E11 was obtained from Dr. R. Putnak (Walter Reed Army Institute of Research, Washington), however an equivalent MAb could be prepared by those skilled in the art. Briefly, DEN-2 NS1 is purified from virally-infected mosquito cells (e.g. $C_{6/36}$ *Aedes albopictis*) using the procedure of Feighny et al ('92). The purified product is combined with Freund's adjuvant and used to immunize mice. Animals exhibiting a strong α-NS 1 response are sacrificed and their splenocytes harvested for polyethylene glycol facilitated fusion with P3×63 g865plasmacytoma cells (ATCC CRL 1580) according to standard procedures (Oi, V. T., L. A. Herzenberg. In Selected Methods in Cellular Immunology Mishell, B. B.; Shiigi, S. M., Eds; W. H. R. Freeman: San Francisco, 1980, Chapter 17). The fusion products are distributed in 96-well microtiter plates and the conditioned media screened for the presence of α-NS1 antibodies by indirect ELISA utilizing wells coated with purified NS1. Positives are subjected to 2–3 rounds of cloning at limiting dilution and then cryopreserved in liquid nitrogen.

EXAMPLE 7

NS1 Augments Immunoprophylactic Activity of 80%E in Mice

The protective capacity of a vaccine combining DEN-2 NS1 and 80%E immunogens was compared to one of identical composition except that NS1 was omitted. 80%E is a C-terminally truncated recombinant fragment of the DEN-2 envelope protein, expressed in Drosophila cells (Coller et al, submitted to Vaccine). Both immunogens were purified by immunoaffinity chromatography facilitated by MAbs 9D12 and 7E11, which are specific for the dengue envelope and NS1 proteins (see Example 6), respectively. Three week old BALB/c (HSD) mice were immunized via the subcutaneous route with adjuvanted preparations of 80%E and 80%E+NS1, as well as negative and positive control groups receiving saline (subcutaneous) and live DEN-2 virus injected intraperitoneally, respectively. For the experimental groups, five μg of each antigen (i.e. 5 μg 80%E and 5 μg 80%E+5 μg NS1) and one fg IscoMatrix™ (IscoTech) adjuvant was used per mouse/injection; primary immunizations were followed a week later by identical boost injections. One week after completion of the immunization schedule, mice were challenged with an intracerebral injection of 100 $LD_{50}$ of mouse-adapted DEN-2 virus. Mortality and morbidity was monitored for 21 days following the viral challenge.

Figure 7:
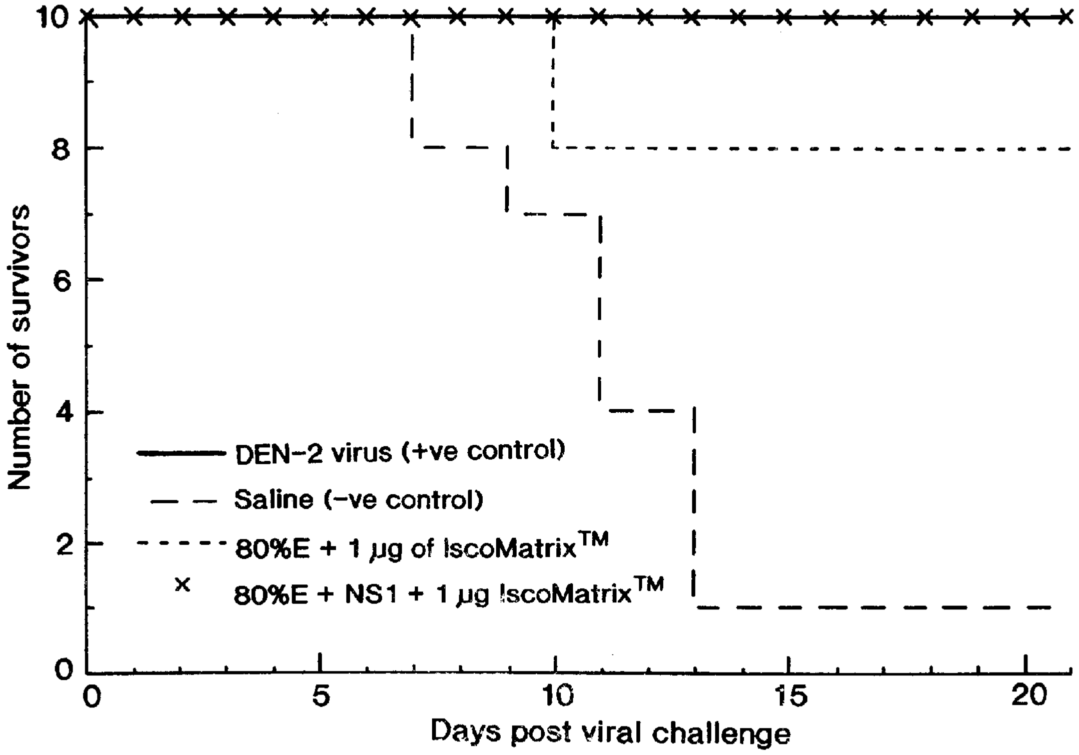
FIG. 7 presents the survival curves of mice immunized with DEN-2 antigens in IscoMatrix™ and challenged intracranially with DEN-2 virus.

Survival curves are shown in FIG. 7. As expected, the positive control intraperitoneal immunization of live DEN-2 virus elicited complete protection, while 9/10 mice mock-immunized with saline were dead within two weeks of the viral challenge. Immunization with 80%E+NS1 also provided complete protection, while 80%E alone prevented death in 8 of 10 animals. In a separate experiment, 5 μg of IAC-purified NS1 plus1 μg IscoMatrix™ protected 6/10 mice, while the positive and negative controls (same as above) provided protection for 10/10 and 2/10 suckling mice, respectively. The absence of any protective effect from IscoMatrix™ adjuvant alone (1 of 10 mice survived) was also demonstrated in this experiment.

The enhanced immunoprophylactic activity of 80%E combined with NS1 does not appear to be adjuvant-dependent as similar results were obtained using Freund's adjuvant rather than IscoMatrix™. NS1 for this experiment was partially purified (~60% of total protein was NS1) via a two-step chromatographic procedure utilizing cation-exchange on cellufine sulfate (Amicon; linear NaCl gradient in 20 mM succinate pH 6.0) followed by DEAE-fractogel anion-exchange (EM Sciences; cellufine sulfate eluate buffer-exchanged into 50 mM NaCl, 16 mM tris/4 mM succinate pH 8.1, bound to DEAE-fractogel and eluted with a linear gradient of increasing NaCl concentration). As above, 80%E for this experiment was purified (~95% of total protein was 80%E) by immunoaffinity chromatography on a column of immobilized 9D 12 MAb. Three week old BALB/c mice were immunized with 25 μg of each antigen (i.e. 25 μg 80%E and 25 μg 80%E+25 μg NS1; weights refer to total amount of protein from each antigen preparation) administered intraperitonially in Freund's complete adjuvant. Booster injections containing half the priming antigen dose were administered i.p. in Freund's incomplete adjuvant 7 and 15 days following the primary immunization. Intracranial challenge with DEN-2 virus was initiated 7 days after the final booster injection and survival monitored for a further 21 days.

Figure 8:
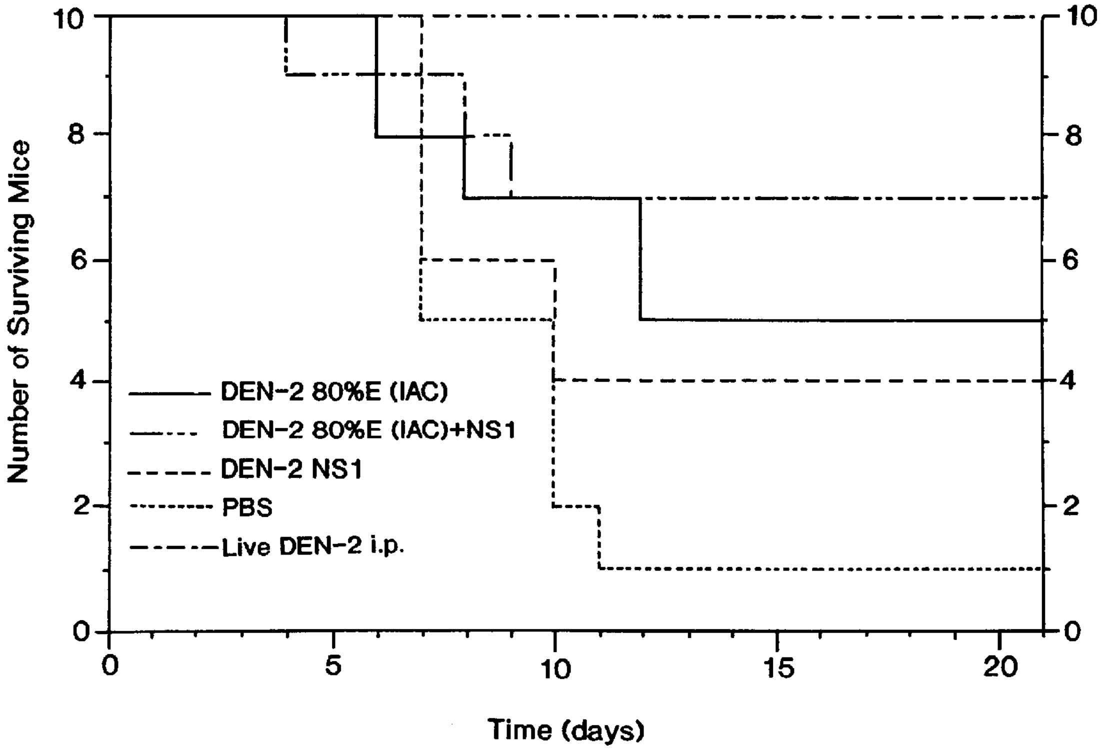
FIG. 8 shows survival curves for mice immunized with DEN-2 antigens in Freund's adjuvant and challenged intracranially with DEN-2 virus.

Survival plots are presented in FIG. 8; as ex.pected, mice immunized with live DEN-2 virus (positive control) were completely protected, while 9 of 10 negative control animals receiving only saline injections succumbed to the viral challenge. Immunization with 80%E conferred protection to 5 of the 10 animals tested, while the surviving fraction was increased to 7 of 10 when NS1 was included in the immunogen. Pre-challenge injection of NS1 alone provided protection in 4/10 stickling mice. Although these data illustrate the augmentative effect of NS1 in a different adjuvant system, it is worth noting that we consistently obtain better immune responses to our recombinant dengue antigens using IscoMatrix™ instead of Freund's adjuvant.

What is claimed is:

1. An immunogenic composition which induces an immunological response in a host subject inoculated with said composition comprising a carrier and a mixture comprising a Flavivirus truncated envelope (E) protein and a Flavivirus nonstructural (NS) protein, wherein said nonstructural protein (NS) protein has been secreted as a recombinantly produced protein, from Drosophila cells, and wherein the truncated envelope (E) protein comprises approximately 80%E, wherein said 80%E represents a portion of the envelope protein that comprises approximately 80% of its length starting from amino acid 1 at its N-terminus.

2. The immunogenic composition of claim 1, wherein said envelope protein (E) protein has been secreted as a recombinantly produced protein from Drosophila cells.

3. The immunogenic composition of claim 1 wherein the non-structural (NS) protein is encoded in a DNA construct operably linked downstream from human tissue plasminogen activator prepropeptide secretion leader ($tPA_L$).

4. The immunogenic composition of claim 1 wherein said Flavivirus is a dengue virus.

5. The immunogenic composition of claim 1 wherein said Drosophila cells are *D. melanogaster* Schneider cells.

6. The immunogenic composition of claim 2 wherein said Drosophila cells are *D. melanogaster* Schneider cells.

7. A method to produce an immunogenic composition comprising (a) culturing the Drosophila cells modified to contain a DNA molecule which comprises
   a nucleotide sequence encoding a nonstructural (NS) protein of the Flavivirus against which enhanced protection is sought in culture medium under conditions favorable for expression of the encoding nucleotide sequence so that the cells secrete said nonstructural (NS) protein of the Flavivirus strain against which enhanced protection is sought;

(b) recovering the nonstructural (NS) protein from the culture medium; and (c) combining said NS with a Flavivirus truncated envelope protein, wherein the truncated envelope (E) protein comprises approximately 80%E, wherein said 80%E represents a portion of the envelope protein that comprises approximately 80% of its length starting from amino acid 1 at its N-terminus.

8. A method to produce an immunogenic composition comprising (a) culturing the Drosophila cells modified to contain a DNA molecule which comprises a nucleotide sequence encoding a nonstructural (NS1) protein of the Flavivirus against which enhanced protection is sought in culture medium under conditions favorable for expression of the encoding nucleotide sequence so that the cells secrete said NS1 protein of the Flavivirus strain against which enhanced protection is sought;

(b) recovering the NS1 protein from the culture medium; and (c) combining said NS1 with a Flavivirus truncated envelope protein, wherein the truncated envelope (E) protein comprises approximately 80%E, wherein said 80%E represents a portion of the envelope protein that comprises approximately 80% of its length starting from amino acid 1 at its N-terminus.

9. The immunogenic composition of claim 1, wherein the nonstructural (NS) protein is NS1.

10. An immunodiagnostic for the detection of a Flavivirus, wherein said immunodiagnostic comprises, the immunogenic composition of claim 1.

11. The immunodiagnostic of claim 10, wherein the nonstructural (NS) protein is NS1.

12. The immunodiagnostic of claim 10, wherein said Flavivirus is a dengue virus.

13. The immunodiagnostic of claim 10, wherein said envelope (E) protein has been secreted as a recombinantly produced protein from Drosophila cells.

14. The immunodiagnostic of claim 13, wherein said Drosophila cells are *D. melanogaster* Schneider cells.

* * * * *